United States Patent [19]
Lerner et al.

[11] Patent Number: 6,060,596
[45] Date of Patent: May 9, 2000

[54] ENCODED COMBINATORIAL CHEMICAL LIBRARIES

[75] Inventors: Richard Lerner, La Jolla; Kim Janda, San Diego, both of Calif.; Sydney Brenner, Edwards Passage, United Kingdom

[73] Assignee: The Scripps Research Institute, La Jolla, Calif.

[21] Appl. No.: 09/033,743

[22] Filed: Mar. 3, 1998

Related U.S. Application Data

[62] Division of application No. 08/665,511, Jun. 18, 1996, Pat. No. 5,723,598, which is a division of application No. 07/860,445, Mar. 30, 1992, Pat. No. 5,573,905.

[51] Int. Cl.[7] ................................................. C07H 21/00
[52] U.S. Cl. .......................................................... 536/25.3
[58] Field of Search ................................ 536/25.3, 24.2; 436/518, 536; 435/6

[56] References Cited

U.S. PATENT DOCUMENTS

| | | | |
|---|---|---|---|
| 4,748,111 | 5/1988 | Dattagupta et al. | 435/6 |
| 4,923,901 | 5/1990 | Koester et al. | 521/53 |
| 4,965,188 | 10/1990 | Mullis et al. | 435/6 |
| 5,082,780 | 1/1992 | Warren et al. | 435/191 |
| 5,141,813 | 8/1992 | Nelson | 428/402 |

FOREIGN PATENT DOCUMENTS

| | | |
|---|---|---|
| 0 323 152 | 5/1989 | European Pat. Off. . |

OTHER PUBLICATIONS

Clontech Laboratories, Inc., *Sales Literature*: 2–3 (1994).
Cwirla, et al., "Peptides on phage: A vast library of peptides for identifying ligands", *Proc. Natl. Acad. Sci. USA 87*: 6378–6382 (1990).
Devlin, et al., "Random Peptide Libraries: A Source of Specific Protein Binding Molecules", *Science 249*: 404–406 (1990).
Fodor, et al., "Light–Directed, Spatially Addressable Parallel Chemical Synthesis", *Science 251*: 767–775 (1991).
Geysen, et al., "Use of peptide synthesis to probe viral antigens for epitopes to a resolution of a single amino acid", *Proc. Natl. Acad. Sci. USA 81*: 3998–4002 (1984).
Houghton, et al., "Generation and use of synthetic peptide combinatorial libraries for basic research and drug discovery", *Nature 354*: 84–86 (1991).
Lam, et al., "A new type of synthetic peptide library for identifying ligand–binding activity", *Nature 354*: 82–84 (1991).
Maeji, et al., "Simultaneous multiple synthesis of peptide–carrier conjugates", *J. Immunol. Met. 146*: 83–90 (1992).
Nelson, et al., "A new and versatile reagent for incorporating multiple primary amines into synthetic oligonucleotides" *Nucleic Acids Research 17*: 7179–7195 (1989).
Nelson, et al., "Oligonucleotide labeling methods 3. Direct labeling of oligonucleotides employing a novel, non–nucleosidic, 2–aminobutyl–1, 3–propanediol backbone", *Nucleic Acids Research 20*: 6253–6259 (1992).
Scott, et al., "Searching for Peptide Ligands with an Epitope Library", *Science 249*: 386–390 (1990).
Hays, et al., "High–Yield Synthesis of Oligoribonucleotides Using o–Nitrobenzyl Protection of 2'–Hydroxyls", *Tetrahedron Letters 26*: 2407–2410 (1985).
Hampel et al. Nucleic Acids Research. vol. 18, No. 2, pp. 299–304, 1990.
Alberts et al., Molecular Biology of the Cell, p. 343. Garland Pubishing, Inc. New York, 1983.

*Primary Examiner*—Remy Yucel
*Attorney, Agent, or Firm*—Thomas E. Northrup

[57] ABSTRACT

The present invention describes an encoded combinatorial chemical library comprised of a plurality of bifunctional molecules having both a chemical polymer and an identifier oligonucleotide sequence that defines the structure of the chemical polymer. Also described are the bifunctional molecules of the library, and methods of using the library to identify chemical structures within the library that bind to biologically active molecules in preselected binding interactions.

17 Claims, 2 Drawing Sheets

ENCODED COMBINATORIAL CHEMICAL LIBRARIES

This application is a divisional of Ser. No. 08/665,511, filed Jun. 18, 1996, now U.S. Pat. No. 5,723,598, which is a divisional of Ser. No. 07/860,445, filed Mar. 30, 1992, now U.S. Pat. No. 5,573,905.

DESCRIPTION

1. Technical Field

The present invention relates to encoded chemical libraries that contain repertoires of chemical structures defining a diversity of biological structures, and methods for using the libraries.

2. Background

There is an increasing need to find new molecules which can effectively modulate a wide range of biological processes, for applications in medicine and agriculture. A standard way for searching for novel bioactive chemicals is to screen collections of natural materials, such as fermentation broths or plant extracts, or libraries of synthesized molecules using assays which can range in complexity from simple binding reactions to elaborate physiological preparations. The screens often only provide leads which then require further improvement either by empirical methods or by chemical design. The process it time-consuming and costly but it is unlikely to be totally replaced by rational methods even when they are based on detailed knowledge of the chemical structure of the target molecules. Thus, what we might call "irrational drug design"—the process of selecting the right molecules from large ensembles or repertoires—requires continual improvement both in the generation of repertoires and in the methods of selection.

Recently there have been several developments in using peptides or nucleotides to provide libraries of compounds for lead discovery. The methods were originally developed to speed up the determination of epitopes recognized by monoclonal antibodies. For example, the standard serial process of stepwise search of synthetic peptides now encompasses a variety of highly sophisticated methods in which large arrays of peptides are synthesized in parallel and screened with acceptor molecules labelled with fluorescent or other reporter groups. The sequence of any effective peptide can be decoded from its address in the array. See for example Geysen et al., *Proc. Natl. Acad. Sci. USA*, 81:3998–4002 (1984); Maeji et al., *J. Immunol. Met.*, 146:83–90 (1992); and Fodor et al., *Science*, 251: 767–775 (1991).

In another approach, Lam et. al., *Nature*, 354:82–84 (1991) describes combinatorial libraries of peptides that are synthesized on resin beads such that each resin bead contains about 20 pmoles of the same peptide. The beads are screened with labelled acceptor molecules and those with bound acceptor are searched for by visual inspection, physically removed, and the peptide identified by direct sequence analysis. In principle, this method could be used with other chemical entities but it requires sensitive methods for sequence determination.

A different method of solving the problem of identification in a combinatorial peptide library is used by Houghten et al., *Nature*, 354:84–86 (1991). For hexapeptides of the 20 natural amino acids, 400 separate libraries are synthesized, each with the first two amino acids fixed and the remaining four positions occupied by all possible combinations. An assay, based on competition for binding or other activity, is then used to find the library with an active peptide. Then twenty new libraries are synthesized and assayed to determine the effective amino acid in the third position, and the process is reiterated in this fashion until the active hexapeptide is defined. This is analogous to the method used in searching a dictionary; the peptide is decoded by construction using a series of sieves or buckets and this makes the search logarithmic.

A very powerful biological method has recently been described in which the library of peptides is presented on the surface of a bacteriophage such that each phage has an individual peptide and contains the DNA sequence specifying it. The library is made by synthesizing a repertoire of random oligonucleotides to generate all combinations, followed by their insertion into a phage vector. Each of the sequences is cloned in one phage and the relevant peptide can be selected by finding those that bind to the particular target. The phages recovered in this way can be amplified and the selection repeated. The sequence of the peptide is decoded by sequencing the DNA. See for example Cwirla et al., *Proc. Natl. Acad. Sci. USA*, 87:6378–6382 (1990); Scott et al., *Science*, 249:386–390 (1990); and Devlin et al., *Science*, 249:404–406 (1990).

Another "genetic" method has been described where the libraries are the synthetic oligonucleotides themselves wherein active oligonucleotide molecules are selected by binding to an acceptor and are then amplified by the polymerase chain reaction (PCR). PCR allows serial enrichment and the structure of the active molecules is then decoded by DNA sequencing on clones generated from the PCR products. The repertoire is limited to nucleotides and the natural pyrimidine and purine bases or those modifications that preserve specific Watson-Crick pairing and can be copied by polymerases.

The main advantages of the genetic methods reside in the capacity for cloning and amplification of DNA sequences, which allows enrichment by serial selection and provides a facile method for decoding the structure of active molecules. However, the genetic repertoires are restricted to nucleotides and peptides composed of natural amino acids and a more extensive chemical repertoire is required to populate the entire universe of binding sites. In contrast, chemical methods can provide limitless repertoires but they lack the capacity for serial enrichment and there are difficulties in discovering the structures of selected active molecules.

BRIEF SUMMARY OF THE INVENTION

The present invention provides a way of combining the virtues of both of the chemical and genetic methods summarized above through the construction of encoded combinatorial chemical libraries, in which each chemical sequence is labelled by an appended "genetic" tag, itself constructed by chemical synthesis, to provide a "retrogenetic" way of specifying each chemical structure.

In outline, two alternating parallel combinatorial syntheses are performed so that the genetic tag is chemically linked to the chemical structure being synthesized; in each case, the addition of one of the particular chemical units to the structure is followed by the addition of an oligonucleotide sequence, which is defined to "code" for that chemical unit, ie., to function as an identifier for the structure of the chemical unit. The library is built up by the repetition of this process after pooling and division.

Active molecules are selected from the library so produced by binding to a preselected biological molecule of interest. Thereafter, the identity of the active molecule is determined by reading the genetic tag, i.e., the identifier oligonucleotide sequence. In one embodiment, amplified copies of their retrogenetic tags can be obtained by the polymerase chain reaction.

The strands of the amplified copies with the appropriate polarity can then be used to enrich for a subset of the library by hybridization with the matching tags and the process can then be repeated on this subset. Thus serial enrichment is achieved by a process of purification exploiting linkage to a nucleotide sequence which can be amplified. Finally, the structure of the chemical entities are decoded by cloning and sequencing the products of the PCR reaction.

The present invention therefore provides a novel method for identifying a chemical structure having a preselected binding activity through the use of a library of bifunctional molecules that provides a rich source of chemical diversity. The library is used to identify chemical structures (structural motifs) that interact with preselected biological molecules.

Thus, in one embodiment, the invention contemplates a bifunctional molecule according to the formula A—B—C, where A is a chemical moiety, B is a linker molecule operatively linked to A and C, and C is an identifier oligonucleotide comprising a sequence of nucleotides that identifies the structure of chemical moiety A.

In another embodiment, the invention contemplates a library comprising a plurality of species of bifunctional molecules, thereby forming a repertoire of chemical diversity.

Another embodiment contemplates a method for identifying a chemical structure that participates in a preselected binding interaction with a biologically active molecule, where the chemical structure is present in the library of bifunctional molecules according to this invention. The method comprises the steps of:

a) admixing in solution the library of bifunctional molecules with the biologically active molecule under binding conditions for a time period sufficient to form a binding reaction complex;
   b) isolating the complex formed in step (a); and
   c) determining the nucleotide sequence of the polymer identifier oligonucleotide in the isolated complex and thereby identifying the chemical structure that participated in the preselected binding interaction.

The invention also contemplates a method for preparing a library according to this invention comprising the steps of:

a) providing a linker molecule B having termini A' and C' according to the formula A'—B—C' that is adapted for reaction with a chemical precursor unit X' at termini A' and with a nucleotide precursor Z' at termini C';
   b) conducting syntheses by adding chemical precursor unit X' to termini A' of said linker and adding precursor unit identifier oligonucleotide Z' to termini C' of said linker, to form a composition containing bifunctional molecules having the structure $X_n$—B—$Z_n$;
   c) repeating step (b) on one or more aliquots of the composition to produce aliquots that contain a product containing a bifunctional molecule;
   d) combining the aliquots produced in step (c) to form an admixture of bifunctional molecules, thereby forming said library.

BRIEF DESCRIPTION OF THE DRAWINGS

In the drawings, forming a portion of this disclosure.

DETAILED DESCRIPTION OF THE INVENTION

A. Encoded Combinatorial Chemical Libraries

Figure 1:
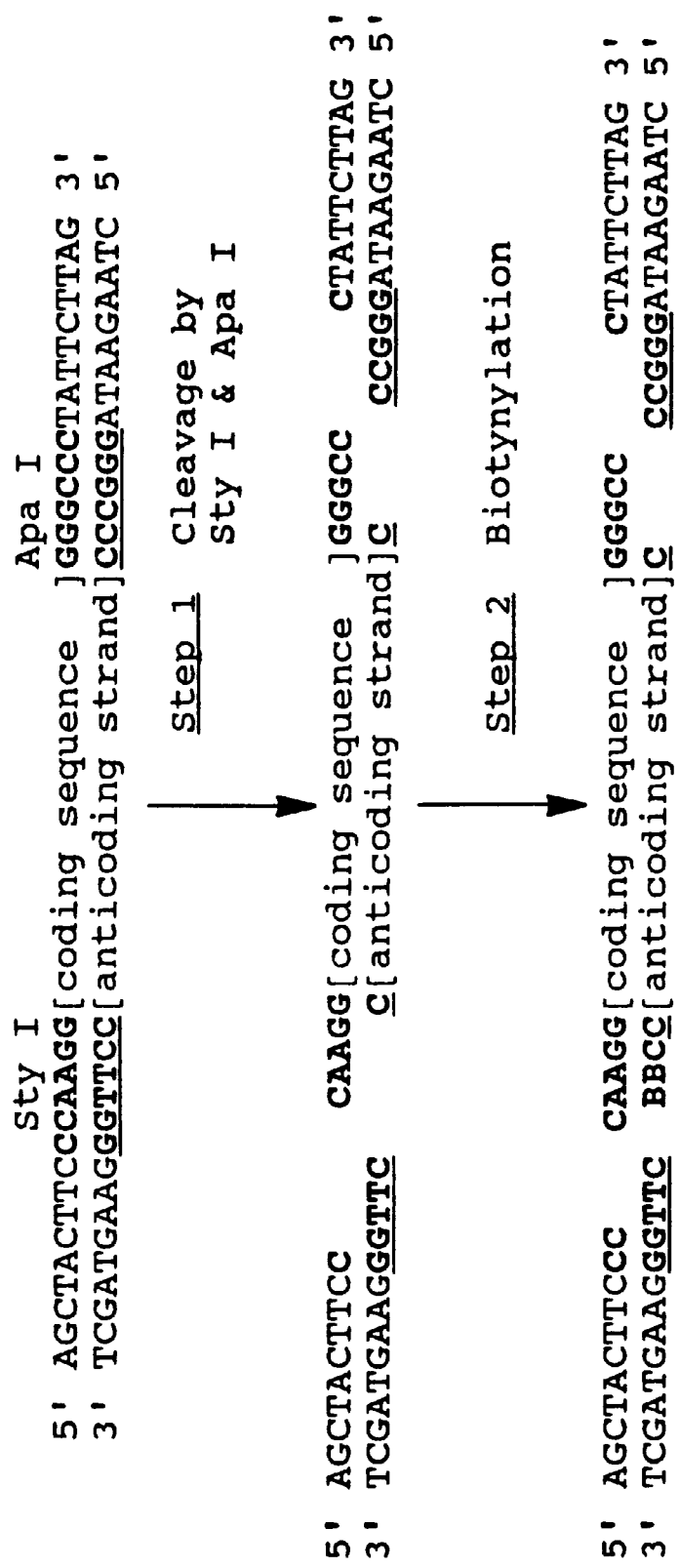
FIG. 1 illustrates a scheme for the restriction endonuclease cleavage of a PCR amplification product derived from a bifunctional molecule of this invention (Step 1), and the subsequent addition of biotin to the cleaved PCR product (Step 2). The unique coding and non-coding nucleotide base sequences shown in FIG. 1 are listed in the Sequence Listing, SEQ ID NOs 15–22.

An encoded combinatorial chemical library is a composition comprising a plurality of species of bifunctional molecules that each define a different chemical structure and that each contain a unique identifier oligonucleotide whose nucleotide sequence defines the corresponding chemical structure.

1. Bifunctional Molecules

A bifunctional molecule is the basic unit in a library of this invention, and combines the elements of a polymer comprised of a series of chemical building blocks to form a chemical moiety in the library, and a code for identifying the structure of the chemical moiety.

Thus, a bifunctional molecule can be represented by the formula A—B—C, where A is a chemical moiety, B is a linker molecule operatively linked to A and C, and C is an identifier oligonucleotide comprising a sequence of nucleotides that identifies the structure of chemical moiety A.

a. Chemical Polymers A chemical moiety in a bifunctional molecule of this invention is represented by A in the above formula A—B—C and is a polymer comprising a linear series of chemical units represented by the formula $(X_n)_a$, wherein X is a single chemical unit in polymer A and n is a position identifier for X in polymer A. n has the value of 1+i where i is an integer from 0 to 10, such that when n is 1, X is located most proximal to the linker (B).

Although the length of the polymer can vary, defined by a, practical library size limitations arise if there is a large alphabet size as discussed further herein. Typically, a is an integer from 4 to 50.

A chemical moiety (polymer A) can be any of a variety of polymeric structures, depending on the choice of classes of chemical diversity to be represented in a library of this invention. Polymer A can be any monomeric chemical unit that can be coupled and extended in polymeric form. For example, polymer A can be a polypeptide, oligosaccharide, glycolipid, lipid, proteoglycan, glycopeptide, sulfonamide, nucleoprotein, conjugated peptide (i.e., having prosthetic groups), polymer containing enzyme substrates, including transition state analogues, and the like biochemical polymers. Exemplary is the polypeptide-based library described herein.

Where the library is comprised of peptide polymers, the chemical unit X can be selected to form a region of a natural protein or can be a non-natural polypeptide, can be comprised of natural D-amino acids, or can be comprised of non-natural amino acids or mixtures of natural and non-natural amino acids.

The non-natural combinations provide for the identification of useful and unique structural motifs involved in biological interactions.

Non-natural amino acids include modified amino acids and L-amino acids, stereoisomer of D-amino acids. The amino acid residues described herein are preferred to be in the "L" isomeric form. NH$_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552–59 (1969) and adopted at 37 C.F.R. §1.822(b)(2)), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

The phrase "amino acid residue" is broadly defined to include the amino acids listed in the Table of Correspondence and modified and unusual amino acids, such as those listed in 37 C.F.R. §1.822(b)(4), and incorporated herein by reference.

The polymer defined by chemical moiety A can therefor contain any polymer backbone modifications that provide increased chemical diversity. In building of a polypeptide system as exemplary, a variety of modifications are contemplated, including the following backbone structures: —NHN(R)CO—, —NHB(R)CO—, —NHC(RR')CO—, —NHC(=CHR)CO—, —NHC$_6$H$_4$CO—, —NHCH$_2$CHRCO—, —NHCHRCH$_2$CO—, and lactam structures.

In addition, amide bond modifications are contemplated including —COCH$_2$—, —COS—, —CONR, —COO—, —CSNH—, —CH$_2$NH—, —CH$_2$CH$_2$—, —CH$_2$S—, —CH$_2$SO—, —CH$_2$SO$_2$—, —CH(CH$_3$)S—, —CH=CH—, —NHCO—, —NHCONH—, —CONHO—, and —C=CH$_2$)CH$_2$—.

b. Polymer Identifier Oligonucleotide

An identifier oligonucleotide in a bifunctional molecule of this invention is represented by C in the above formula A—B—C and is an oligonucleotide having a sequence represented by the formula $(Z_n)_a$, wherein Z is a unit identifier nucleotide sequence within oligonucleotide C that identifies the chemical unit X at position n. n has the value of 1+i where i is an integer from 0 to 10, such that when n is 1, Z is located most proximal to the linker (B). a is an integer as described previously to connote the number of chemical unit identifiers in the oligonucleotide.

For example, a bifunctional molecule can be represented by the formula:

$X_4X_3X_2X_1$—B—$Z_1Z_2Z_3Z_4$.

In this example, the sequence of oligonucleotides $Z_1$, $Z_2$, $Z_3$ and $Z_4$ identifies the structure of chemical units $X_1$, $X_2$, $X_3$ and $X_4$, respectively. Thus, there is a correspondence in the identifier sequence between a chemical unit X at position n and the unit identifier oligonucleotide Z at position n.

The length of a unit identifier oligonucleotide can vary depending on the complexity of the library, the number of different chemical units to be uniquely identified, and other considerations relating to requirements for uniqueness of oligonucleotides such as hybridization and polymerase chain reaction fidelity. A typical length can be from about 2 to about 10 nucleotides, although nothing is to preclude a unit identifier from being longer.

Insofar as adenosine (A), guanosine (G), thymidine (T) and cytosine (C) represent the typical choices of nucleotides for inclusion in a unit identifier oligonucleotide, A, G, T and C form a representative "alphabet" used to "spell" out a unit identifier oligonucleotide's sequence. Other nucleotides or nucleotide analogs can be utilized in addition to or in place of the above four nucleotides, so long as they have the ability to form Watson-Crick pairs and be replicated by DNA polymerases in a PCR reaction. However, the nucleotides A, G, T and C are preferred.

For the design of the code in the identifier oligonucleotide, it is essential to chose a coding representation such that no significant part of the oligonucleotide sequence can occur in another unrelated combination by chance or otherwise during the manipulations of a bifunctional molecule in the library.

For example, consider a library where Z is a trinucleotide whose sequence defines a unique chemical unit X. Because the methods of this invention provide for all combinations and permutations of an alphabet of chemical units, it is possible for two different unit identifier oligonucleotide sequences to have closely related sequences that differ by only a frame shift and therefore are not easily distinguishable by hybridization or sequencing unless the frame is clear.

Other sources of misreading of a unit identifier oligonucleotide can arise. For example, mismatch in DNA hybridization, transcription errors during a primer extension reaction to amplify or sequence the identifier oligonucleotide, and the like errors can occur during a manipulation of a bifunctional molecule.

The invention contemplates a variety of means to reduce the possibility of error in reading the identifier oligonucleotide, such as to use longer nucleotide lengths for a unit identifier nucleotide sequence as to reduce the similarity between unit identifier nucleotide sequences. Typical lengths depend on the size of the alphabet of chemical units.

A representative system useful for eliminating read errors due to frame shift or mutation is a code developed as a theoretical alternative to the genetic code and is known as the commaless genetic code.

Where the chemical units are amino acids, a convenient unit identifier nucleotide sequence is the well known genetic code using triplet codons. The invention need not be limited by the translation afforded between the triplet codon of the genetic code and the natural amino acids; other systems of correspondence can be assigned.

A typical and exemplary unit identifier nucleotide sequence is based on the commaless code having a length of six nucleotides (hexanucleotide) per chemical unit.

Preferably, an identifier oligonucleotide has at least 15 nucleotides in the tag (coding) region for effective hybridization. In addition, considerations of the complexity of the library, the size of the alphabet of chemical units, and the length of the polymer length of the chemical moiety all contribute to length of the identifier oligonucleotide as discussed in more detail herein.

In a preferred embodiment, an identifier oligonucleotide C has a nucleotide sequence according to the formula P1—$(Z_n)_a$—P2, where P1 and P2 are nucleotide sequences that provide polymerase chain reaction (PCR) primer binding sites adapted to amplify the polymer identifier oligonucleotide. The requirements for PCR primer binding sites are generally well known in the art, but are designed to allow a PCR amplification product (a PCR-amplified duplex DNA fragment) to be formed that contains the polymer identifier oligonucleotide sequences.

The presence of the two PCR primer binding sites, P1 and P2, flanking the identifier oligonucleotide sequence $(Z_n)_a$ provides a means to produce a PCR-amplified duplex DNA fragment derived from the bifunctional molecule using PCR. This design is useful to allow the amplification of the tag sequence present on a particular bifunctional molecule for cloning and sequencing purposes in the process of reading the identifier code to determine the structure of the chemical moiety in the bifunctional molecule.

More preferred is a bifunctional molecule where one or both of the nucleotide sequences P1 and P2 are designed to contain a means for removing the PCR primer binding sites from the identifier oligonucleotide sequences. Removal of the flanking Pi and P2 sequences is desirable so that their sequences do not contribute to a subsequent hybridization reaction. Preferred means for removing the PCR primer binding sites from a PCR amplification product is in the form of a restriction endonuclease site within the PCR-amplified duplex DNA fragment.

Restriction endonucleases are well known in the art and are enzymes that recognize specific lengths of duplex DNA and cleave the DNA in a sequence-specific manner.

Preferably, the restriction endonuclease sites should be positioned proximal to $(Z_n)_a$ relative to the PCR primer binding sites to maximize the amount of P1 and P2 that is removed upon treating a bifunctional molecule to the specific restriction endonuclease. More preferably, P1 and P2 each are adapted to form a restriction endonuclease site in the resulting PCR-amplified duplex DNA, and the two restriction sites, when cleaved by the restriction endonuclease, form non-overlapping cohesive termini to facilitate subsequent manipulations.

Particularly preferred are restriction sites that when cleaved provide overhanging termini adapted for termini-specific modifications such as incorporation of a biotinylated nucleotide (e.g., biotinyl deoxy-UTP) to facilitate subsequent manipulations.

The above described preferred embodiments in an identifier oligonucleotide are summarized in a specific embodiment shown in FIG. 1.

In FIG. 1, a PCR-amplified duplex DNA is shown that is derived from an identifier oligonucleotide described in the Examples. The $(Z_n)$ sequence is illustrated in the brackets as the coding sequence and its complementary strand of the duplex is indicated in the brackets as the anticoding strand. The P1 and P2 sequences are shown in detail with a Sty I restriction endonuclease site defined by the P1 sequence located 5' to the bracket and an Apy I restriction endonuclease site defined by the P2 sequence located 3' to the bracket.

Step 1 illustrates the cleavage of the PCR-amplified duplex DNA by the enzymes Sty I and Apa I to form a modified identifier sequence with cohesive termini. Step 2 illustrates the specific biotinylation of the anticoding strand at the Sty I site, whereby the incorporation of biotinylated UTP is indicated by a B.

The presence of non-overlapping cohesive termini after Step 1 in FIG. 1 allows the specific and directional cloning of the restriction-digested PCR-amplified fragment into an appropriate vector, such as a sequencing vector. In addition, the Sty I was designed into Pi because the resulting overhang is a substrate for a filling-in reaction with dCTP and biotinyl-dUTP (BTP) using DNA polymerase Klenow fragment. The other restriction site, Apa I, was selected to not provide substrate for the above biotinylation, so that only the anticoding strand can be biotinylated.

Once biotinylated, the duplex fragment can be bound to immobilized avidin and the duplex can be denatured to release the coding sequence containing the identifier nucleotide sequence, thereby providing purified anticoding strand that is useful as a hybridization reagent for selection of related coding strands as described further herein.

c. Linker Molecules

A linker molecule in a bifunctional molecule of this invention is represented by B in the above formula A—B—C and can be any molecule that performs the function of operatively linking the chemical moiety to the identifier oligonucleotide.

Preferably, a linker molecule has a means for attaching to a solid support, thereby facilitating synthesis of the bifunctional molecule in the solid phase. In addition, attachment to a solid support provides certain features in practicing the screening methods with a library of bifunctional molecules as described herein. Particularly preferred are linker molecules in which the means for attaching to a solid support is reversible, namely, that the linker can be separated from the solid support.

A linker molecule can vary in structure and length, and provide at least two features: (1) operative linkage to chemical moiety A, and (2) operative linkage to identifier oligonucleotide C. As the nature of chemical linkages is diverse, any of a variety of chemistries may be utilized to effect the indicated operative linkages to A and to C, as the nature of the linkage is not considered an essential feature of this invention. The size of the linker in terms of the length between A and C can vary widely, but for the purposes of the invention, need not exceed a length sufficient to provide the linkage functions indicated. Thus, a chain length of from at least one to about 20 atoms is preferred.

A preferred linker molecule is described in Example 3 herein that contains the added, preferred, element of a reversible means for attachment to a solid support. That is, the bifunctional molecule is removable from the solid support after synthesis.

Solid supports for chemical synthesis are generally well known. Particularly preferred are the synthetic resins used in oligonucleotide and in polypeptide synthesis that are available from a variety of commercial sources including Glen Research (Herndon, Va.), Bachem Biosciences, (Philadelphia, Pa.), and Applied Biosystems (Foster City, Calif.). Most preferred are teflon supports such as that described in Example 2.

2. Libraries

A library of this invention is a repertoire of chemical diversity comprising a plurality of species of bifunctional molecules according to the present invention. The plurality of species in a library defines a family of chemical diversity whose species each have a different chemical moiety. Thus the library can define a family of peptides, lipids, oligosaccarides or any of the other classes of chemical polymers recited previously.

The number of different species in a library represents the complexity of a library and is defined by the polymer length of the chemical moiety, and by the size of the chemical unit alphabet that can be used to build the chemical unit polymer. The number of different species referred to by the phrase "plurality of species" in a library can be defined by the formula $V^a$, i.e., V to power of a (exponent a). V represents the alphabet size, i.e., the number of different chemical units X available for use in the chemical moiety. "a" is an exponent to V and represents the number of chemical units of X forming the polymer A, i.e., the length of polymer A.

For example, for a bifunctional molecule where polymer A is a peptide having a length of 6 amino acids, and where the amino acids utilized can be any of the 20 natural amino acids, the alphabet (V) is 20 and the polymer length (a) is 6, and the library size is $20^6$ or 64 million. This exemplary library provides a repertoire of chemical diversity comprising 64 million different hexameric polypeptides operatively linked to corresponding unique identifier oligonucleotides.

Because the complexity of the library will determine the amount of a particular species of bifunctional molecule relative the other species in the library, there are theoretical limits to the maximum useful complexity in a library. Therefore it is useful to consider how large (complex) a library should be. This size limit is dictated by the level of sensitivity for detecting the presence of a polymer identifier oligonucleotide after a screening procedure according to this invention. Detection sensitivity is dictated by the threshold of binding between an acceptor molecule to be assayed and a bifunctional molecule.

If, for example, the binding threshold is $10^{-6}M$ (micromolar), then there must be at least one nanomole of each species in a library of 1 milliliter (ml) volume. At this threshold, a library having a complexity of $10^4$ could contain 10 micromoles of each species. Because of the reciprocal relationship between library complexity and binding threshold, more complex libraries are possible where the binding threshold is lower.

The relative amounts of the individual bifunctional molecule species within the library can vary from about 0.2 equivalents to about 10 equivalents, where an equivalent represents the average amount of a species within the library. Preferably each species is present in the library in approximately equimolar amounts.

In a preferred embodiment, a library contains the complete repertoire of chemical diversity possible based on the mathematical combinations for a given library where there is a fixed alphabet and a preselected number of chemical units in all species of the library. Thus a complete repertoire is one that provides a source of all the possible chemical diversity that can be found in a library of this invention having a fixed alphabet and chemical length.

It is particularly preferred that a library be comprised of bifunctional molecules where each species of bifunctional molecule contains the same nucleotide sequence for either the P1 or P2 PCR primer binding sites. A library with this design is particularly preferred because, when practicing the methods of this invention, a single PCR primer pair can be used to amplify any species of identifier oligonucleotide (coding sequence) present in the library.

B. Methods for Producing a Library

The present method for producing a plurality of bifunctional molecules to form a library of this invention solves a variety of problems regarding efficient synthesis of large numbers of different species.

In the present synthesis methods, the sequential steps of first adding a chemical unit X followed by the addition of an oligonucleotide sequence to the linker molecule requires an alternating parallel synthesis procedure to add chemical unit X and then add a unit identifier nucleotide sequence Z that defines (codes for) that corresponding chemical unit. The library is built up by the repetition of this alternating parallel process after pooling and division of the reaction products as described herein.

The only constraint for making an encoded library is that there must be compatible chemistries between the two alternating syntheses procedures for adding a chemical unit as compared to that for adding a nucleotide or oligonucleotide sequence.

The problem of synthesis compatibility is solved by the correct choice of compatible protecting groups as the alternating polymers are synthesized, and by the correct choice of methods for deprotection of one growing polymer selectively while the other growing polymer remains blocked.

The synthesis of a library having a plurality of bifunctional molecules comprises the following steps:

(1) A linker molecule is provided that has suitable means for operatively linking the first chemical unit $X_1$ and for operatively linking the first nucleotide sequence defining a unit identifier nucleotide $Z_1$ whose sequence codes for (defines) the structure of chemical unit $X_1$. Preferably the linker has a means for attachment to a solid support, and as such allows for the synthesis to proceed in the solid phase.

Thus the provided linker molecule has a structure A'—B—C', where A' represents a termini adapted for reaction to operatively link a chemical unit X in precursor form (X'), and C' represents a termini adapted for reaction to operatively link a nucleotide or polymer identifier oligonucleotide Z in precursor form (Z'). The termini A' and C' are protected by respective blocking groups so that during operative linking reactions at one termini, the other termini is protected from reaction.

(2) The linker molecule is then subjected to a first cycle of synthesis to add a building block at one termini. The order of synthesis is not generally important insofar as one may elect to add a chemical unit X first to termini A', or add an identifier oligonucleotide Z first to termini C'. A first cycle involves the steps of deprotecting the termini of the linker to which a building block is to be added and then adding the building block to the termini. Typically, the added building block contains a blocking group at its free termini, i.e., the termini that will participate in an addition of the next building block of its type. The linker molecule is then subjected to a second cycle of synthesis to add a building block at the other (second) termini. A second cycle involves the steps of deprotecting the second termini of the linker to which a building block is to be added and then adding the building block to the termini. Again, the added building block is typically blocked at its free termini.

The addition of identifier oligonucleotide Z to termini C' can be conducted either nucleotide by nucleotide to form the complete unit identifier nucleotide sequence Z, or Z can be presynthesized, and the oligonucleotide Z added as a block to termini C'. Insofar as the synthesis of oligonucleotides is well known in the arts, the presynthesis of oligonucleotides, and their addition to the growing nucleotide polymer in blocks is preferred because it reduces the number of manipulations in synthesizing a bifunctional molecule.

A chemical unit X or a unit identifier oligonucleotide Z is referred to as a precursor (X' or Z') to indicate that it contains a leaving group compatible with the reaction chemistry that facilitates the precursor's operative linkage to the growing polymer at the appropriate termini.

The product resulting from step (2) is a bifunctional molecule having the structure A'—$X_1$—B—$Z_1$—C', and is ready for a repetition of the above first and second cycles to add $X_2$ and $Z_2$ to the growing polymers.

(3) After the bifunctional molecule product A'—$X_1$—B—$Z_1$—C' is formed, aliquots of the product are made, and the cycles in step (2) are repeated on each aliquot, with the exception that a different species of X (and its corresponding Z) is added in each different aliquot. The reaction product in each aliquot has the structure A'—$X_2$—$X_1$—B—$Z_1$—$Z_2$—C'.

(4) The aliquots each containing the product A'—$X_2$—$X_1$—B—$Z_1$—$Z_2$—C' are combined (pooled) to form a mixture of different bifunctional molecules, and the mixture is divided into aliquots. The cycles in step (2) are repeated again on each aliquot, with different X and Z building blocks being added to each aliquot to form the bifunctional molecule product A—'$X_3$—$X_2$—$X_1$—B—$Z_1$—$Z_2$—$Z_3$—C'.

The process of pooling, aliquoting and adding a next set of building blocks X and Z can be repeated at positions n=4, 5, 6 . . . and so on depending on the length of polymers desired. As the cycles are repeated, and the polymers grow in length, the complexity of the resulting library also increases. For each cycle, the polymer length a increases by one and the library complexity therefore increases exponentionally according to the formula $V^a$. In preferred embodiments, the cycles are repeated from about 1 to 10 times.

In a related embodiment the provided linker in step (1) is first divided into aliquots, and the cycles of step (2) are conducted on each aliquot adding a different X and corresponding Z to the linker in each different aliquot. The aliquots are then pooled as before, and the cycles of step (2) can be repeated on one or more aliquots.

Thus the steps of (i) dividing a linker or pool into aliquots, (ii) parallel addition of X and Z to the linker substrate in separate aliquots, and (iii) pooling of the aliquots, can be cycled (repeated) to sequentially add the chemical units and their corresponding unit identifier oligonucleotides to form the library comprising a plurality of bifunctional molecules each having a different chemical polymer operatively linked through the linker to a corresponding identifier oligonucleotide.

In a preferred embodiment, a method for forming a library of this invention includes the steps for addition of the PCR primer binding sites P1 and P2 to each of the bifunctional molecules in the library.

The method is substantially the same as above, but includes the addition of a series of nucleotides or a presynthesized P1 oligonucleotide to the linker molecule provided in step (1) prior to the cycles of step (2) that add X and Z. Because all members of the library are to contain the same P1 sequence, P1 is added to the C' termini of linker molecule A'—B—C' prior to dividing the linker into aliquots and subjecting the aliquots to the cycles of step (2) adding $X_1$ and $Z_1$. The resulting product has the formula A'—B—P1—C'.

Thereafter, the product is aliquoted and cycled as before, resulting in the preparation of the product A'—$(X_n)_a$—B—P1—$(Z_n)_a$—C', where a indicates the presence of a polymer of length "a".

Next, the pooled admixture containing product A'—$(X_n)_a$—B—P1—$(Z_n)_a$—C' is subjected to the addition of a series of nucleotides or a presynthesized oligonucleotide P2 at termini C' to form the product A'—$(X_n)_a$—B—P1—$(Z_n)_a$—P2—C' Thus all members of the library contain a common sequence P1 and a common sequence P2 from which universal PCR reactions can be conducted, regardless of the species of bifunctional molecule present from the library.

1. Polypeptide Libraries

In one preferred embodiment, the invention contemplates a library, and methods of producing the library, where the bifunctional molecule has a polypeptide for polymer A.

In this embodiment, the compatible chemistries for sequentially adding amino acids and oligonucleotides to the growing polymers has been developed for the synthesis of an amino acid polymer in the direction of carboxy to amino terminus, and alternatively in the direction of amino to carboxy terminus. Chemistries have also been developed for the synthesis of an oligonucleotide polymer in the direction of 3' to 5', and alternatively in the direction of 5' to 3'. In addition, in each of these syntheses it is preferred that the amino acid side chains (R groups) be blocked for certain amino acid residues where the R group provides an otherwise reactive termini during one of the synthesis or deblocking steps.

Each type of chemistry will be described in detail herein below.

For any of the syntheses, the reactive side chains of several amino acids must be blocked. Table 1 below lists those of the natural amino acids which have an R group that preferably contains a blocking group. Any compatible protecting (blocking) group may be utilized, and the invention is not to be so limited to any particular blocking group. Also indicated in Table 1 are preferred blocking groups.

TABLE 1

| Amino Acid | Blocking Group |
| --- | --- |
| Arginine | N-MTr[1], N-PMC[7] |
| Histidine | $N^\pi$-Bum[2] |
| Cysteine | S-Trt[3] |
| Tryptophan | $N^i$-CHO |
| Tyrosine | O-TBS[4] |
| Aspartic acid | O-TSE[5] |
| Glutamic acid | O-TSE[5] |
| Serine | O-TBS[4] |
| Threonine | O-TBS[4] |
| Lysine | N-Bz[6] |
| Asparagine | |
| Glutamine | |

Protected amino acids suitable as a blocked precursor for addition to a bifunctional molecule can be obtained from a variety of commercial vendors including Bachem Biosciences Inc. (Philadelphia, Pa.), Peninsula Labs (CA), and Nova Biochem (CA). In addition, the preparation of protected amino acids is described in Example 1.

a. Polypeptide Synthesis

For synthesis of a polypeptide on the linker substrate in the direction of carboxy to amino terminus, a free amino terminus on the linker is required that can be conveniently blocked and deblocked as needed. A preferred amino terminus blocking group is a fluromethoxycarbonyl group (FMOC).

FMOC blocked amino termini are deblocked with (DBU) in dichloromethane (DCM) as is well known for polypeptide synthesis. The amino acid units are added in the form of blocked amino acids having FMOC blocked amino termini and a carboxyl terminus blocked with pentafluorophenyl ester (Opfp). The addition reaction requires the blocked amino acid, dimethylformamide (DMF) and hydroxybenzotriazole (HOBt) as is well known for peptide synthesis. The resulting product contains an added amino acid residue with a FMOC-blocked amino terminus, ready for deblocking addition of a subsequent blocked amino acid as before.

For synthesis of a polypeptide on the linker substrate in the direction of amino to carboxy terminus, a free carboxy terminus on the linker is required that can be conveniently blocked and deblocked as needed. A preferred carboxy terminus blocking group is the Opfp ester described before. A carboxy terminus on the linker is produced by reacting a linker with a free amino terminus with succinamide in HOBE and a proton catalyst. Thereafter, the terminus can be modified by reaction with pentafluorophenol in dichlorocarbodiimide (DCC) and ethanol acetate to form an Opfp ester at the free carboxy terminus. The Opfp ester is blocked linker terminus is available for addition reaction with a FMOC-, Opfp-blocked amino acid as before, but with the amino acid adding to the linker in the reverse direction. The resulting product contains an added amino acid residue with an Opfp-blocked terminus, ready to repeat the addition with a subsequent blocked amino acid.

b. Oligonucleotide Synthesis

Oligonucleotides can be synthesized by a variety of chemistries as is well known. An excellent review is "Oligonucleotide Synthesis: A Practical Approach", ed. M. J. Gait, JRL Press, New York, N.Y. (1990).

For synthesis of an oligonucleotide on the linker substrate in the direction of 3' to 5', a free hydroxy terminus on the linker is required that can be conveniently blocked and deblocked as needed. A preferred hydroxy terminus blocking group is a dimexothytrityl ether (DMT). DMT blocked termini are first deblocked, such as by treatment with 3% dichloroacetic acid in dichloromethane (DCM) as is well known for oligonucleotide synthesis, to form a free hydroxy terminus.

Nucleotides in precursor form for addition to a free hydroxy terminus in the direction of 3' to 5' require a phosphoramidate moiety having an aminodiisopropyl side chain at the 3' terminus of a nucleotide. In addition, the free hydroxy of the phosphoramidate is blocked with a cyanoethyl ester (OCNET), and the 5' terminus is blocked with a DMT ether.

The addition of a 5' DMT-, 3' OCNET-blocked phosphoramidate nucleotide to a free hydroxyl requires tetrazole in acetonitrile followed by iodine oxidation and capping of unreacted hydroxyls with acetic anhydride, as is well known for oligonucleotide synthesis. The resulting product contains an added nucleotide residue with a DMT blocked 5' terminus, ready for deblocking and addition of a subsequent blocked nucleotide as before.

For synthesis of an oligonucleotide on the linker in the direction of 51 to 3', a free hydroxy terminus on the linker is required as before. However, the blocked nucleotide to be added has the blocking chemistries reversed on its 5' and 3' termini to facilitate addition in the opposite orientation.

A nucleotide with a free 3' hydroxyl and 5' DMT ether is first blocked at the 3' hydroxy terminus by reaction with TBS-Cl in imidazole to form a TBS ester at the 3' terminus. Then the DMT-blocked 5' terminus is deblocked with DCA in DCM as before to form a free 5' hydroxy terminus. The reagent (N,N-diisopropylamino)(cyanoethyl) phosphonamidic chloride having an aminodiisopropyl group and an OCNET ester is reacted in tetrahydrofuran (THF) with the 5' deblocked nucleotide to form the aminodiisopropyl-, OCNET-blocked phosphonamidate group on the 5' terminus. Thereafter the 3' TBS ester is removed with tetrabutylammonium fluoride (TBAF) in DCM to form a nucleotide with the phosphonamidate-blocked 5' terminus and a free 3' hydroxy terminus. Reaction in base with DMT-Cl adds a DMT ether blocking group to the 3' hydroxy terminus.

The addition of the 3' DMT-, 5' OCNET-blocked phosphonamidated nucleotide to a linker substrate having a free hydroxy terminus then proceeds using the previous tetrazole reaction, as is well known for oligonucleotide polymerization. The resulting product contains an added nucleotide residue with a DMT-blocked 3' terminus, ready for deblocking with DCA in DCM and the addition of a subsequent blocked nucleotide as before.

The above demonstrates that the present bifunctional molecules can be synthesized having polypeptide $(X)_a$ in either orientation and having the polymer identifier oligonucleotide $(Z)_a$ in either orientation. Exemplary is the synthesis described herein in detail to form a library of bifunctional molecules having the oligonucleotide attached to linker through its 3' terminus and having the peptide attached to linker through its carboxy terminus.

In one preferred embodiment, the order of synthesis orients the polypeptide on the linker such that after addition an added amino acid has a free amino terminus, that is, the polymer is assembled in the direction from carboxy to amino terminus. Exemplary chemistry for this synthesis is described in the Examples.

The addition of oligonucleotides rather than single nucleotides to the growing polymer identifier nucleotide sequence is an alternate embodiment that is preferred because it affords more rapid and modular assembly of the library. Although the previous synthesis discussions involved single nucleotide base units, the same blocking groups and addition chemistries apply where an oligonucleotide is to be added.

The synthesis of a oligonucleotide having 5' OCNET-blocked and 3' DMT-blocked termini or having 3' OCNET-blocked and 5' DMT-blocked termini can readily be prepared using the oligonucleotide synthesis methods presently available and described herein.

After synthesis of a bifunctional molecule, or library of molecules, the blocking groups at termini and at amino acid side chains are removed. Because of the relative lability of termini, it is preferred that the order of deblocking be selected as to preserve the functionalities, particularly the side chain functionalities.

In the present preferred embodiment for a polypeptide library, the following sequence of deprotecting is preferred:
1) tetrabutyl ammonium fluoride (TBAF) treatment to remove TBS and TMS ethyl ethers;
2) tetrafluoroacetic (TFA) treatment to remove MTr, Bum, PMC and Trt groups;
3) aqueous ammonia treatments to remove Bz and OCNET groups; and
4) cleavage of the bifunctional molecule from the solid support using a periodate oxidation.

As indicated, after the library has been synthesized, and after the protecting groups have been removed, the bifunctional molecules may be cleaved off of the solid support, and the released bifunctional molecules separated from the solid phase to form a solution comprising a plurality of bifunctional molecules. Alternatively, the library may be maintained in the form of a plurality of bifunctional molecules in the solid phase.

Although natural amino acids are used in the Examples, the present invention is not to be so limited. The alphabet of possible amino acid residues can be extended to include any molecule that satisfies the basic chemistry defining an amino acid, namely carboxyl and amino termini. Upon polymerization, an amide bond is formed. Thus the possible amino acids can include L-amino acids, D-amino acids, natural amino acids, non-natural amino acids, and derivatives thereof.

In addition, there is no basis to limit the polypeptide backbone connecting the termini to the conventional amino acid structure. The amino and carboxylic acid moieties can be on any backbone having any side group substituents, so long as the side groups are properly blocked as described herein. Previously undescribed amino acids may be developed that can be used in the present invention, having unusual heterocyclic rings, such as thiazole-alanine or purine alanine.

The development and use of both conventional and unusual amino acid structures provide a greater diversity of chemical moieties for a library of this invention. Such libraries allow the exploration by the screening methods of this invention of new combinations of important core chemical structures.

Typical backbones can be alkyl chains of $(CH_2)_n$ where n can be from 1 to at least 6. In addition, the alphabet can comprise amino acids of varying backbone structures. Alphabets can also comprise amino acids where the number of carbon atoms and their configuration in the backbone can be varied.

C. Methods for Identifying Chemical Structures

The library of this invention provides a repertoire of chemical diversity such that each chemical moiety is linked to a genetic tag that facilitates identification of the chemical structure.

By the present screening methods, one can identify optimized chemical structures that participate in binding interactions with a biologically active molecule by drawing upon a repertoire of structures randomly formed by the combinatorial association of diverse chemical units without the necessity of either synthesizing them one at a time or knowing their interactions in advance.

The invention therefore also contemplates a method for identifying a chemical structure that participates in a preselected binding interaction between the chemical structure and a biologically active molecule. The chemical structure to be identified is represented by one of the members of a library of this invention, and the method comprises the following steps:

(1) A library according to the present invention is admixed with a preselected biologically active molecule under binding conditions (i.e., a binding reaction admixture) for a time period sufficient for the biologically active molecule to interact with at least one bifunctional molecule of this invention present in the library and form a binding reaction complex.

(2) The binding reaction complex is then isolated from the library admixture to form an isolated complex.

(3) The nucleotide sequence of the polymer identifier oligonucleotide present in the isolated binding reaction complex is determined. The nucleotide sequence provides a code that defines the chemical structure that participated in the binding reaction, and thus determining that sequence identifies the chemical structure that participates in the binding reaction with the biologically active molecule.

A typical biologically active molecule exhibiting a preselected binding interaction can be any of a variety of molecules that bind selectively to another molecule, including antibodies to antigens, lectins to oligosaccharides, receptors to ligands, enzymes to substrates and the like mediators of molecular interactions. Therefore, a preselected binding interaction is defined by the selection of the biologically active molecule with which a library member is to bind.

1. Binding Reaction Admixtures

The admixture of a library of the invention with a biologically active molecule can be in the form of a heterogeneous or homogeneous admixture. Thus, the members of the library can be in the solid phase with the biologically active molecule present in the liquid phase. Alternatively, the biologically active molecule can be in the solid phase with the members of the library present in the liquid phase. Still further, both the library members and the biologically active molecule can be in the liquid phase.

Binding conditions are those conditions compatible with the known natural binding function of the biologically active molecule. Those compatible conditions are buffer, pH and temperature conditions that maintain the biological activity of the biologically active molecule, thereby maintaining the ability of the molecule to participate in its preselected binding interaction. Typically, those conditions include an aqueous, physiologic solution of pH and ionic strength normally associated with the biologically active molecule of interest.

For example, where the binding interaction is to identify a member in the library able to bind an antibody molecule, the preferred binding conditions would be conditions suitable for the antibody to immunoreact with its immunogen, or a known immunoreacting antigen. For a receptor molecule, the binding conditions would be those compatible with measuring receptor-ligand interactions.

A time period sufficient for the admixture to form a binding reaction complex is typically that length of time required for the biologically active molecule to interact with its normal binding partner under conditions compatible with interaction. Although the time periods can vary depending on the molecule, admixing times are typically for at least a few minutes, and usually not longer than several hours, although nothing is to preclude using longer admixing times for a binding reaction complex to form.

A binding reaction complex is a stable product of the interaction between a biologically active molecule and a bifunctional molecule of this invention. The product is referred to as a stable product in that the interaction is maintained over sufficient time that the complex can be isolated from the rest of the members of the library without the complex becoming significantly disassociated.

2. Isolation of a Bifunctional Molecule from the Binding Reaction Admixture

A binding reaction complex is isolated from the binding reaction admixture by any separation means that is selective for the complex, thereby isolating that species of bifunctional molecule which has bound to the biologically active molecule. There are a variety of separation means, depending on the status of the biologically active molecule.

For example, the biologically active molecule can be provided in admixture in the form of a solid phase reagent, i.e., affixed to a solid support, and thus can readily be separated from the liquid phase, thereby removing the majority of species of bifunctional molecule. Separation of the solid phase from the binding reaction admixture can optionally be accompanied by washes of the solid support to rinse bifunctional molecules having lower binding affinities off of the solid support.

Alternatively, for a homogeneous liquid binding reaction admixture, a secondary binding means specific for the biologically active molecule can be utilized to bind the molecule and provide for its separation from the binding reaction admixture.

For example, an immobilized antibody immunospecific for the biologically active molecule can be provided as a solid phase-affixed antibody to the binding reaction admixture after the binding reaction complex is formed. The immobilized antibody immunoreacts with the biologically active molecule present in the binding reaction admixture to form an antibody-biologically active molecule immunoreaction complex. Thereafter, by separation of the solid phase from the binding reaction admixture, the immunoreaction complex, and therefor any binding reaction complex, is separated from the admixture to form isolated bifunctional molecule.

Alternatively, a binding means can be operatively linked to the biologically active molecule to facilitate its retrieval from the binding reaction admixture. Exemplary binding means are one of the following high affinity pairs: biotin-avidin, protein A-Fc receptor, ferritin-magnetic beads, and the like. Thus, the biologically active molecule is operatively linked (conjugated) to biotin, protein A, ferritin and the like binding means, and the binding reaction complex is isolated by the use of the corresponding binding partner in the solid phase, e.g., solid-phase avidin, solid-phase Fc receptor, solid phase magnetic beads and the like.

The use of solid supports on which to operatively link proteinaceous molecules is generally well known in the art. Useful solid support matrices are well known in the art and include cross-linked dextran such as that available under the tradename SEPHADEX from Pharmacia Fine Chemicals (Piscataway, N.J.); agarose, borosilicate, polystyrene or latex beads about 1 micron to about 5 millimeters in diameter, polyvinyl chloride, polystyrene, cross-linked polyacrylamide, nitrocellulose or nylon-based webs such as sheets, strips, paddles, plates microtiter plate wells and the like insoluble matrices.

3. Determining the Identifier Sequence

The nucleotide sequence of the identifier oligonucleotide present in the isolated bifunctional molecules is determined to identify the species of chemical moiety that participated in the preselected binding interaction.

Although conventional DNA sequencing methods are readily available and useful for this determination, the amount and quality of isolated bifunctional molecule may require additional manipulations prior to a sequencing reaction.

Where the amount is low, it is preferred to increase the amount of the identifier oligonucleotide by polymerase chain reaction (PCR) using PCR primers directed to the primers P1 and P2 present in the identifier oligonucleotide.

In addition, the quality of the isolated bifunctional molecule may be such that multiple species of bifunctional molecule are co-isolated by virtue of similar capacities for binding to the biologically active molecule. In cases where more than one species of bifunctional molecule are isolated, the different isolated species must be separated prior to sequencing of the identifier oligonucleotide.

Thus in one embodiment, the different identifier oligonucleotides of the isolated bifunctional molecules are cloned into separate sequencing vectors prior to determining their sequence by DNA sequencing methods. This is typically accomplished by amplifying all of the different identifier oligonucleotides by PCR as described herein, and then using the unique restriction endonuclease sites on the amplified product as shown in FIG. 1 to directionally clone the amplified fragments into sequencing vectors. The cloning and sequencing of the amplified fragments then is a routine procedure that can be carried out by any of a number of molecular biological methods known in the art.

Alternatively, PCR amplified products derived from a population of isolated bifunctional molecules can be used as a hybridization probe to selectively enrich the quality of the isolated bifunctional molecules. For example, using the hybridization probes, which are modified by biotinylation as shown in FIG. 1, one can isolate members of the library by hybridization, to form an enriched library containing only bifunctional molecules that have sequences that hybridize to the above hybridization probes. In a second screening reaction under different binding conditions, for example, higher stringency binding conditions, one can isolate the species of bifunctional molecule that binds most tightly with the biologically active molecule.

Thus the library can be manipulated to form enriched libraries from which to screen for chemical diversity.

4. Polymerase Chain Reaction

For determining the nucleotide sequence of the identifier oligonucleotide in the isolated complex as part of the methods of this invention, the use of the polymerase chain reaction (PCR) is a preferred embodiment.

For use in this invention, the identifier oligonucleotide are comprised of polynucleotide coding strands, such as mRNA and/or the sense strand of genomic DNA. If the genetic material to be assayed is in the form of double stranded DNA, it is usually first denatured, typically by melting, into single strands. The nucleic acid is subjected to a PCR reaction by treating (contacting) the sample with a PCR primer pair, each member of the pair having a preselected nucleotide sequence. The PCR primer pair is capable of initiating primer extension reactions by hybridizing to the PCR primer binding site on nucleotide sequences of the identifier nucleotide, preferably at least about 10 nucleotides in length, more preferably at least about 20 nucleotides in length and most preferably 17 nucleotides in length. The first primer of a PCR primer pair is sometimes referred to herein as the "anti-sense primer" because it hybridizes to a non-coding or anti-sense strand of a nucleic acid, i.e., a strand complementary to a coding strand. The second primer of a PCR primer pair is sometimes referred to herein as the "sense primer" because it hybridizes to the coding or sense strand of a nucleic acid.

The PCR reaction is performed by mixing the PCR primer pair, preferably a predetermined amount thereof, with the nucleic acids of the sample, preferably a predetermined amount thereof, in a PCR buffer to form a PCR reaction admixture. The admixture is thermocycled for a number of cycles, which is typically predetermined, sufficient for the formation of a PCR reaction product, thereby enriching the sample to be assayed for the identifier oligonucleotide in the isolated complex.

PCR is typically carried out by thermocycling i.e., repeatedly increasing and decreasing the temperature of a PCR reaction admixture within a temperature range whose lower limit is about 30 degrees Celsius (30° C.) to about 55° C. and whose upper limit is about 90° C. to about 100° C. The increasing and decreasing can be continuous, but is preferably phasic with time periods of relative temperature stability at each of temperatures favoring polynucleotide synthesis, denaturation and hybridization.

A plurality of first primer and/or a plurality of second primers can be used in each amplification, e.g., one species of first primer can be paired with a number of different second primers to form several different primer pairs. Alternatively, an individual pair of first and second primers can be used. In any case, the amplification products of amplifications using the same or different combinations of first and second primers can be combined for assaying for mutations.

The PCR reaction is performed using any suitable method. Generally it occurs in a buffered aqueous solution, i.e., a PCR buffer, preferably at a pH of 7–9, most preferably about 8. Preferably, a molar excess of the primer is admixed to the buffer containing the template strand. A large molar excess is preferred to improve the efficiency of the process.

The PCR buffer also contains the deoxyribonucleotide triphosphates (polynucleotide synthesis substrates) dATP, dCTP, dGTP, and dTTP and a polymerase, typically thermostable, all in adequate amounts for primer extension (polynucleotide synthesis) reaction. The resulting solution (PCR admixture) is heated to about 90° C.–100° C. for about 1 to 10 minutes, preferably from 1 to 4 minutes. After this heating period the solution is allowed to cool to 54° C., which is preferable for primer hybridization. The synthesis reaction may occur at from room temperature up to a temperature above which the polymerase (inducing agent) no longer functions efficiently. Thus, for example, if DNA polymerase is used as inducing agent, the temperature is generally no greater than about 40° C. The thermocycling is repeated until the desired amount of PCR product is produced. An exemplary PCR buffer comprises the following: 50 mM KCl; 10 mM Tris-HCl at pH 8.3; 1.5 mM $MgCl_2$; 0.001% (wt/vol) gelatin, 200 $\mu$M dATP; 200 $\mu$M dTTP; 200 $\mu$M dCTP; 200 $\mu$M dGTP; and 2.5 units Thermus aquaticus (Taq) DNA polymerase I (U.S. Pat. No. 4,889,818) per 100 microliters ($\mu$l) of buffer.

The inducing agent may be any compound or system which will function to accomplish the synthesis of primer extension products, including enzymes. Suitable enzymes for this purpose include, for example, E. coli DNA polymerase I, Klenow fragment of E. coli DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above.

The inducing agent also may be a compound or system which will function to accomplish the synthesis of RNA primer extension products, including enzymes. In preferred embodiments, the inducing agent may be a DNA-dependent RNA polymerase such as T7 RNA polymerase, T3 RNA polymerase or SP6 RNA polymerase. These polymerases produce a complementary RNA polynucleotide. The high turn-over rate of the RNA polymerase amplifies the starting polynucleotide as has been described by Chamberlin et al., The Enzymes, ed. P. Boyer, pp. 87–108, Academic Press, New York (1982). Amplification systems based on transcription have been described by Gingeras et al., in PCR Protocols, A Guide to Methods and Applications, pp. 245–252, Innis et al., eds, Academic Press, Inc., San Diego, Calif. (1990).

If the inducing agent is a DNA-dependent RNA polymerase and, therefore incorporates ribonucleotide triphosphates, sufficient amounts of ATP, CTP, GTP and UTP are admixed to the primer extension reaction admixture and the resulting solution is treated as described above.

The newly synthesized strand and its complementary nucleic acid strand form a double-stranded molecule which can be used in the succeeding steps of the process.

PCR amplification methods are described in detail in U.S. Pat. Nos. 4,683,192, 4,683,202, 4,800,159, and 4,965,188, and at least in several texts including PCR Technology: Principles and Applications for DNA Amplification, H. Erlich, ed., Stockton Press, New York (1989); and PCR Protocols: A Guide to Methods and Applications, Innis et al., eds., Academic Press, San Diego, Calif. (1990).

The term "polynucleotide" as used herein in reference to primers, probes and nucleic acid fragments or segments to be synthesized by primer extension is defined as a molecule comprised of two or more deoxyribonucleotides or ribonucleotides, preferably more than three. Its exact size will depend on many factors, which in turn depends on the ultimate conditions of use.

The term "primer" as used herein refers to a polynucleotide whether purified from a nucleic acid restriction digest or produced synthetically, which is capable of acting as a point of initiation of nucleic acid synthesis when placed under conditions in which synthesis of a primer extension product which is complementary to a nucleic acid strand is induced, i.e., in the presence of nucleotides and an agent for polymerization such as DNA polymerase, reverse transcriptase and the like, and at a suitable temperature and pH. The primer is preferably single stranded for maximum efficiency, but may alternatively be in double stranded form. If double stranded, the primer is first treated to separate it from its complementary strand before being used to prepare extension products. Preferably, the primer is a polydeoxyribonucleotide. The primer must be sufficiently long to prime the synthesis of extension products in the presence of the agents for polymerization. The exact lengths of the primers will depend on many factors, including temperature and the source of primer. For example, depending on the complexity of the target sequence, a polynucleotide primer typically contains 15 to 25 or more nucleotides, although it can contain fewer nucleotides. Short primer molecules generally require cooler temperatures to form sufficiently stable hybrid complexes with template.

The primers used herein are selected to be "substantially" complementary to the different strands of each specific sequence to be synthesized or amplified. This means that the primer must be sufficiently complementary to non-randomly hybridize with its respective template strand. Therefore, the primer sequence may or may not reflect the exact sequence of the template. For example, a non-complementary nucleotide fragment can be attached to the 5' end of the primer, with the remainder of the primer sequence being substantially complementary to the strand. Such non-complementary fragments typically code for an endonuclease restriction site. Alternatively, non-complementary bases or longer sequences can be interspersed into the primer, provided the primer sequence has sufficient complementarity with the sequence of the strand to be synthesized or amplified to non-randomly hybridize therewith and thereby form an extension product under polynucleotide synthesizing conditions.

Primers of the present invention may also contain a DNA-dependent RNA polymerase promoter sequence or its complement. See for example, Krieg et al., Nucl. Acids Res., 12:7057–70 (1984); Studier et al., J. Mol. Biol., 189:113–130 (1986); and Molecular Cloning: A Laboratory Manual, Second Edition, Maniatis et al., eds., Cold Spring Harbor, N.Y. (1989).

When a primer containing a DNA-dependent RNA polymerase promoter is used, the primer is hybridized to the polynucleotide strand to be amplified and the second polynucleotide strand of the DNA-dependent RNA polymerase promoter is completed using an inducing agent such as E. coli DNA polymerase I, or the Klenow fragment of E. coli DNA polymerase. The starting polynucleotide is amplified by alternating between the production of an RNA polynucleotide and DNA polynucleotide.

Primers may also contain a template sequence or replication initiation site for a RNA-directed RNA polymerase.

Typical RNA-directed RNA polymerase include the QB replicase described by Lizardi et al., *Biotechnology*, 6:1197–1202 (1988). RNA-directed polymerases produce large numbers of RNA strands from a small number of template RNA strands that contain a template sequence or replication initiation site. These polymerases typically give a one million-fold amplification of the template strand as has been described by Kramer et al., *J. Mol. Biol.*, 89:719–736 (1974).

The polynucleotide primers can be prepared using any suitable method, such as, for example, the phosphotriester or phosphodiester methods see Narang et al., *Meth. Enzymol.*, 68:90, (1979); U.S. Pat. No. 4,356,270, U.S. Pat. No. 4,458,066, U.S. Pat. No. 4,416,988, U.S. Pat. No. 4,293,652; and Brown et al., *Meth. Enzymol.*, 68:109, (1979).

If the nucleic acid sample is to be enriched for the identifier oligonucleotide in the isolated complex by PCR amplification, two primers, i.e., a PCR primer pair, must be used for each coding strand of nucleic acid to be amplified. The first primer becomes part of the non-coding (anti-sense or minus or complementary) strand and hybridizes to a nucleotide sequence on the plus or coding strand. Second primers become part of the coding (sense or plus) strand and hybridize to a nucleotide sequence on the minus or non-coding strand. One or both of the first and second primers can contain a nucleotide sequence defining an endonuclease recognition site as described herein. The site can be heterologous to the polymer identifier oligonucleotide being amplified.

In one embodiment, the present invention utilizes a set of polynucleotides that form primers having a priming region located at the 3'-terminus of the primer. The priming region is typically the 3'-most (3'-terminal) 15 to 30 nucleotide bases. The 3'-terminal priming portion of each primer is capable of acting as a primer to catalyze nucleic acid synthesis, i.e., initiate a primer extension reaction off its 3' terminus. One or both of the primers can additionally contain a 5'-terminal (5'-most) non-priming portion, i.e., a region that does not participate in hybridization to the preferred template.

5. Nucleic Acid Sequence Analysis

Nucleic acid sequence analysis is a well known procedure for determining the sequence of nucleotides and is applied to the present methods to determine the nucleotide sequence in an identifier oligonucleotide or PCR amplification product of this invention. Nucleic acid sequence analysis is approached by a combination of (a) physiochemical techniques, based on the hybridization or denaturation of a probe strand plus its complementary target, and (b) enzymatic reactions with endonucleases, ligases, and polymerases.

In assays using nucleic acid hybridization, detecting the presence of a DNA duplex in a process of the present invention can be accomplished by a variety of means.

In one approach for detecting the presence of a DNA duplex, an oligonucleotide that is hybridized in the DNA duplex includes a label or indicating group that will render the duplex detectable. Typically such labels include radioactive atoms, chemically modified nucleotide bases, and the like.

The oligonucleotide can be labeled, i.e., operatively linked to an indicating means or group, and used to detect the presence of a specific nucleotide sequence in a target template.

Radioactive elements operatively linked to or present as part of an oligonucleotide probe (labeled oligonucleotide) provide a useful means to facilitate the detection of a DNA duplex. A typical radioactive element is one that produces beta ray emissions. Elements that emit beta rays, such as $^3$H, $^{12}$C, $^{32}$P and $^{35}$S represent a class of beta ray emission-producing radioactive element labels. A radioactive polynucleotide probe is typically prepared by enzymatic incorporation of radioactively labeled nucleotides into a nucleic acid using DNA kinase.

Alternatives to radioactively labeled oligonucleotides are oligonucleotides that are chemically modified to contain metal complexing agents, biotin-containing groups, fluorescent compounds, and the like.

One useful metal complexing agent is a lanthanide chelate formed by a lanthanide and an aromatic beta-diketone, the lanthanide being bound to the nucleic acid or oligonucleotide via a chelate-forming compound such as an EDTA-analogue so that a fluorescent lanthanide complex is formed. See U.S. Pat. No. 4,374,120, U.S. Pat. No. 4,569,790 and published Patent Application Nos. EP0139675 and W087/02708.

Biotin or acridine ester-labeled oligonucleotides and their use to label polynucleotides have been described. See U.S. Pat. No. 4,707,404, published Patent Application EP0212951 and European Patent No. 0087636. Useful fluorescent marker compounds include fluorescein, rhodamine, Texas Red, NBD and the like.

A labeled oligonucleotide present in a DNA duplex renders the duplex itself labeled and therefore distinguishable over other nucleic acids present in a sample to be assayed. Detecting the presence of the label in the duplex and thereby the presence of the duplex, typically involves separating the DNA duplex from any labeled oligonucleotide probe that is not hybridized to a DNA duplex.

Techniques for the separation of single stranded oligonucleotide, such as non-hybridized labeled oligonucleotide probe, from DNA duplex are well known, and typically involve the separation of single stranded from double stranded nucleic acids on the basis of their chemical properties. More often separation techniques involve the use of a heterogeneous hybridization format in which the non-hybridized probe is separated, typically by washing, from the DNA duplex that is bound to an insoluble matrix. Exemplary is the Southern blot technique, in which the matrix is a nitrocellulose sheet and the label is $^{32}$p. Southern, J. Mol. Biol., 98:503 (1975).

The oligonucleotides can also be advantageously linked, typically at or near their 5'-terminus, to a solid matrix, i.e., aqueous insoluble solid support as previously described.

It is also possible to add "linking" nucleotides to the 5' or 3' end of the member oligonucleotide, and use the linking oligonucleotide to operatively link the member to the solid support.

In nucleotide hybridizing assays, the hybridization reaction mixture is maintained in the contemplated method under hybridizing conditions for a time period sufficient for the oligonucleotides having complementarity to the predetermined sequence on the template to hybridize to complementary nucleic acid sequences present in the template to form a hybridization product, i.e., a complex containing oligonucleotide and target nucleic acid.

The phrase "hybridizing conditions" and its grammatical equivalents, when used with a maintenance time period, indicates subjecting the hybridization reaction admixture, in the context of the concentrations of reactants and accompanying reagents in the admixture, to time, temperature and pH conditions sufficient to allow one or more oligonucleotides to anneal with the target sequence, to form a nucleic acid duplex. Such time, temperature and pH conditions required to accomplish hybridization depend, as is well known in the art, on the length of the oligonucleotide to be hybridized, the degree of complementarity between the oligonucleotide and the target, the guanine and cytosine content of the oligonucleotide, the stringency of hybridization desired, and the presence of salts or additional reagents in the hybridization reaction admixture as may affect the kinetics of hybridization. Methods for optimizing hybridization conditions for a given hybridization reaction admixture are well known in the art.

Typical hybridizing conditions include the use of solutions buffered to pH values between 4 and 9, and are carried out at temperatures from 4° C. to 37° C., preferably about 12° C. to about 30° C., more preferably about 22° C., and for time periods from 0.5 seconds to 24 hours, preferably 2 minutes (min) to 1 hour. Exemplary are the conditions described in Example 4.

Hybridization can be carried out in a homogeneous or heterogeneous format as is well known. The homogeneous hybridization reaction occurs entirely in solution, in which both the oligonucleotide and the nucleic acid sequences to be hybridized (target) are present in soluble forms in solution. A heterogeneous reaction involves the use of a matrix that is insoluble in the reaction medium to which either the oligonucleotide, polynucleotide probe or target nucleic acid is bound.

Where the nucleic acid containing a target sequence is in a double stranded (ds) form, it is preferred to first denature the dsDNA, as by heating or alkali treatment, prior to conducting the hybridization reaction. The denaturation of the dsDNA can be carried out prior to admixture with a oligonucleotide to be hybridized, or can be carried out after the admixture of the dsDNA with the oligonucleotide.

Effective amounts of the oligonucleotide present in the hybridization reaction admixture are generally well known and are typically expressed in terms of molar ratios between the oligonucleotide to be hybridized and the template. Preferred ratios are hybridization reaction mixtures containing equimolar amounts of the target sequence and the oligonucleotide. As is well known, deviations from equal molarity will produce hybridization reaction products, although at lower efficiency. Thus, although ratios where one component can be in as much as 100 fold molar excess relative to the other component, excesses of less than 50 fold, preferably less than 10 fold, and more preferably less than two fold are desirable in practicing the invention.

EXAMPLES

The following examples are intended to illustrate, but not limit, the present invention.

1. Preparation of Protected Amino Acids

The synthesis of a bifunctional molecule requires protected amino acids. The amino-terminus of the amino acid is protected with fluoromethoxycarbonyl (FMOC) and the carboxy-terminus is protected with a pentafluorophenyl ester (Opfp). The amino acids lysine, cysteine, tyrosine, serine, threonine, arginine, histidine, tryptophan, aspartate, and glutamate, require additional protection of their side chains (R groups).

Most of the FMOC and Opfp protected amino acids are commercially available and were obtained from Bachem Biosciences, Inc. (Philadelphia, Pa.). The terminology used herein for their structure is indicated by the following example for glycine (Gly): FMOC-Gly-Opfp, where FMOC and Opfp are the amino and carboxy terminal protecting groups. For side chain protection, the following protected amino acids are available from Bachem: FMOC-Arg (MTr)-Opfp having the substituent $N^9$-4-methoxy-2,3,6-trimethylbenzene sulfonyl arginine (MTr) at the side chain amino terminus of arginine; FMOC-His(Bum)-Opfp having the substituent $N^\pi$-tert-butoxymethylhistidine (Bum) at the heterocyclic reactive nitrogen in histidine; FMOC-Cys(Trt)-Opfp having the substituent S-triphenyl methyl cysteine at the side chain sulfur of cysteine; FMOC-Trp(N-For)-Opfp having a formyl group at the amino group of tryptophan's heterocyclic group; and FMOC-Lys(N-Bz)-Opfp having a benzyl group on the free amino group of lysine's side chain; where the structure in parenthesis indicates the protecting group on the reactive side chain.

FMOC-Tyr(OTBS)-Opfp having a tertbutyldimethysilyl (TBS)ester on the side chain hydroxy of tyrosine is prepared by reacting an excess of formic acid with FMOC-Tyr(tert-butyl)-Opfp (Bachem) to remove the tert butyl group from the protected hydroxyl group to form FMOC-Tyr-Opfp. Thereafter, one equivalent of FMOC-Tyr-Opfp is reacted with 1.2 equivalents of TBS-Cl and 1.5 equivalents of imidazole in DCM at room temperature for 12 hours under inert atmosphere to form FMOC-Tyr(OTBS)-Opfp.

FMOC-Ser(OTBS)-Opfp is similarly prepared using FMOC-Ser(tert-butyl)-Opfp (Bachem) in the reaction. FMOC-Thr(OTBS)-Opfp is also prepared in this manner using FMOC-Thr(tert-butyl)-Opfp (Bachem).

FMOC-Asp(TMSE)-Opfp having a trimethylsilyl ethyl ester (TMSE) on the side chain carboxyl group of aspartic acid is prepared by first reacting one equivalent of FMOC-Asp-O-tertbutyl (Bachem) with 1.5 equivalents of 2-trimethylsilylethanol and 1.5 equivalents if dicyclocarbodiimide (DCC) in ethanol acetate for 12 hours at room temperature under inert atmosphere to form FMOC-Asp (OTMSE)-O-tertbutyl. There after the TMSE ester is reacted with an excess of formic acid at room temperature for 14 hours to hydrolyze the tertbutyl moiety and form a free carboxyl terminus in the form of FMOC-Asp(OTMSE)-COOH. The formic acid is evaporated, and the 1 equivalent of the remaining amino acid is admixed with 1.1 equivalent of pentafluorophenol (pfp; Bachem) and 1.1 equivalent of DCC for 12 hours at room temperature under inert atmosphere to form the product FMOC-Asp(TMSE)-Opfp. The product is isolated from unreacted pfp, DCC and precursor amino acid by silica gel chromatography using 10% (v/v) ethyl acetate in hexane.

FMOC-Glu(TMSE)-Opfp having a TMSE ester on the side chain carboxyl group of glutamic acid is prepared as described above to prepare FMOC-,TMSE- and pfp protected aspartic acid, except that FMOC-Glu-O-tert-butyl (Bachem) is used in place of the aspartic acid precursor, to form FMOC-Glu(TMSE)-Opfp.

2. Preparation of Solid Support

A solid support designated N6-(5'-O-dimethyoxytrityl-2', 3'-diacetyl 1-adenylyl)-teflon support was obtained from Glen Research (Herndon, Va.). The solid support is a teflon resin with a modified adenine nucleoside having the solid support linkage through the 6-amino group of a purine base, a dimethoxytrityl ether (DMT) at the 5' position of the ribose ring and acetate esters at the 2' and 3' positions of the ribose ring. The solid support was admixed with 5 volumes of 3% (v/v) dichloroacetic acid in dichloromethane (3% DCA in DCM) and maintained for 10 minutes at room temperature under inert atmosphere to remove the dimethoxytrityl (DMT) protecting group to form a free 5'hydroxyl. The resulting deprotected solid support was washed 3 times with DCM to remove the excess unreacted DCA. The deprotected washed solid support is ready for coupling to linker.

3. Coupling of Linker to Solid Support

One equivalent of deprotected washed solid support (prepared in Example 2) was admixed with 20 equivalents of a linker designated (1-dimethoxytrityloxy-3-fluorenyl methoxycarbonylamino propan-2yl)-(2-cyanoethyl)-(N,N-diisopropyl)-phosphoramidite and referred to as 5' Branched-Modifier C3 (or 5'BMC3; available from Glen Research) and 20 equivalents of tetrazole (0.45M in acetonitrile, Glen Research) and was agitated with stirring for 0.5 to 1 hour at room temperature to under inert atmosphere. The admixture was then washed with an excess of acetonitrile to remove unreacted reagents. The washed solid phase material was retained and admixed with 2 equivalents of Iodine in tetrahydrofuran/water, 9:1, (available from Glen Research) under inert atmosphere and maintained at room temperature for 10 minutes to form oxidized solid-support coupled linker.

One equivalent of oxidized solid support-coupled linker was then admixed with 20 equivalents of acetonitrile/acetic anhydride, 88:12, (capping reagent; Glen Research) for 10 minutes at room temperature to cap any unreacted free hydroxyls present on the solid support.

4. Coupling of Nucleotide to Solid Support a. Deprotect DMT

The capped solid support-coupled linker prepared in Example 3 was admixed with 3% DCA in DCM for 10 minutes at room temperature under inert atmospheres to remove the DMT protecting group from the linker and form a free hydroxyl group. The deprotected linker/support was then washed 3 times with DCM. The deprotected linker/support is ready for addition of nucleotide.

b. Addition of Nucleotide

One equivalent of deprotected linker/support was admixed with about 20 equivalents of a desired blocked nucleotide phosphoramidite and 20 equivalents of tetrazole (0.45M in acetonitrile) to form a coupled nucleotide/linker/support (coupled nucleotide complex). The coupled nucleotide complex was then washed with an excess of acetonitrile to remove unreacted reagents. All blocked nucleotide phosphoramidites were obtained from Glen Research and contain a DMT protected blocked 5'hydroxyl, a cyanoethyl ester (OCNET) and a diisopropyl amine group at the 3'-phosphoramidate. In addition, the adenine and cytosine derivatives contained a benzoyl group on the base's free nitrogen and the guanosine derivative contains an isobutyl group on the 2-amino group of the purine base.

One equivalent of coupled nucleotide complex was then admixed with 2 equivalents of Iodine in tetrahydrofuran/water, 9:1, for oxidation as before in Example 3 to oxidize the coupled nucleotide complex.

Thereafter, one equivalent of oxidized nucleotide complex was admixed with 20 equivalents of capping reagent as before in Example 3 to cap any unreacted free hydroxyls and to form capped solid phase-coupled nucleotide complex.

5. Coupling of Amino Acid to Solid Support a. Deprotect Nucleotide Complex

One equivalent of capped solid phase-coupled nucleotide complex was admixed with 1 equivalent of 1,8,diazabicyclo[5.4.0]undec-7-ene (DBU) in DCM (available from Aldrich Chemical Co., Milwaukee, Wis.) under inert atmosphere for 10 minutes at room temperature to remove (deblock) the fluoromethoxycarbonyl (FMOC) protecting group from the linker in the nucleotide complex. The deprotected nucleotide complex was then washed with excess DCM to remove unreacted DBU and form a deprotected nucleotide complex with a free amino group.

b. Addition of Amino Acid

One equivalent of deprotected nucleotide complex from Example 5A was admixed with 20 equivalents of protected amino acid in dimethylformamide (DMF) and 20 equivalents of 1-hydroxy-benzotriazole (HOBt) under inert atmosphere for 0.5 to 1 hour at room temperature. This reaction condition couples the carboxy-terminus of the amino acid via its pentafluoropheny ester to the free amino group of the nucleotide complex to form a nucleotide/amino acid 1-conjugate (the conjugate). The conjugate was then washed in excess DCM to remove unreacted HOBt and the precursor amino acid. The protected amino acid is one of those as described in Example 1, having FMOC and Opfp at the amino and carboxy terminus, and if needed, a blocking group on the side chain as described before.

6. Elongation of the Conjugate

The conjugate can be lengthened by alternating cycles of addition of nucleotides and amino acids. The following alternating cycles are repeated until the conjugate has desired length amino acid polymer and oligonucleotide polymer.

a. Addition of Nucleotides

To couple an additional nucleotide, the 5'—OH on the terminal nucleotide is deprotected with DCA following the protocol described previously in Example 4A for the deprotection of the linker/support. Thereafter, a protected nucleotide is added as described in Example 4B.

b. Addition of Amino Acids

To couple an additional amino acid, the amino-FMOC terminus of the last amino acid added to the conjugate is deprotected with DBU as described previously in Example 5A. Thereafter, a protected amino acid is added as described in Example 5B.

The cycle of Steps 1 and 2 above adding alternate nucleotides and amino acids can be repeated until the conjugate has polymers of the desired length and structure.

7. Removal of Protecting Groups

After complete synthesis of one or more bifunctional molecules, the protecting groups are removed from the terminal nucleotide, from the terminal amino acid, and from the side chains of protected amino acids.

a. Removal of Nucleotide Protecting Group

The DMT protecting group on the 5'—OH of the last nucleotide of the oligonucleotide polymer is removed with DCA following the protocol described previously in Example 4A.

b. Removal of Amino Acid Protecting Group

The FMOC protecting group on the amino-terminus of the last amino acid of the amino acid polymer is removed with DBU as described previously in Example 5A.

c. Removal of Amino Acid Side Chain Protecting Group

Conditions for removal of an amino acid side chain protecting group depends on the particular protecting group as follows:

i. Removal of TBS and TSE ester Groups

One unit of the conjugate is admixed with about 20 equivalents of tetrabutylammonium fluoride (TBAF) in DCM and maintained at room temperature under inert atmosphere overnight to remove the TBS or TMSE ethers protecting the side chains of tyrosine, aspartic acid, glutamic acid, serine, and threonine.

ii. Removal of the Bz Group

The conjugate is admixed with an excess of aqueous ammonia and maintained at 60° C. overnight under inert atmosphere to remove the benzyl (Bz) group protecting the side chain amino group of lysine.

iii. Removal of the MTr, Bum and Tpm Groups

The conjugate is admixed with 20 to 50 percent TFA and maintained at room temperature for about 15 minutes under inert atmosphere to remove the MTr, Bum or Tpm groups protecting the side chains of arginine, histidine or cysteine, respectively.

iv. Removal of the Formyl Group

The conjugate is admixed with aqueous buffer at pH 12 and maintained at room temperature for about 5 minutes under inert atmosphere to remove the formyl group protecting the reactive 2-amino group of tryptophan.

8. Cleavage of Conjugate from Solid Support

After the protecting groups are removed from the conjugate, the bifunctional molecule is removed from the solid support by admixing the conjugate with a cleaving solution of 100 mM sodium periodate, 100 mM sodium phosphate buffer, pH 7.2, in acetonitrile/water (1:4 v/v). The admixture is maintained with agitation at room temperature with exclusion of light. After 4 hours of agitation, the liquid phase removed and the solid support is washed with excess water and methanol. The wash solutions are then removed and 1 umole of solid support are admixed with 50 ul n-propylamine, 100 ul acetonitrile and 400 ul water and maintained at 55° C. for 3 hours. Thereafter, the liquid phase is recovered, evaporated to dryness in vacuo, and the dried product is dissolved in acetonitrile/water. The dissolved product is purified using reverse phase HPLC on an EM LiChrospher 100RP-18 m 50 um column (4×25) HPLC column. The mobile phase A is 95% 0.1 TEAA buffer (pH 7.0) and 5% acetonitrile, and mobile phase B is 5% TEAA buffer (pH 7.0) and 95 % acetonitrile. The gradient is 100% A for 5 min, 100% A to 50% for 50 min, with a flow rate of 1 mL per min. The homogeneous fraction is collected to yield a solution of pure bifunctional molecule.

The solution is dialyzed as needed to change the buffer of the purified material.

9. Preparation of a Library of Bifunctional Molecules

Using the synthetic procedures of Examples 1–8, the methods for producing a bifunctional molecule are detailed. To form a library of molecules, additional manipulations are required. First, the synthesis is conducted including the steps of aliquoting, adding different units to each aliquot, and pooling the aliquots to sequentially build the library. Second, if desired, the PCR primer binding sites and the unit identifier oligonucleotides can be added as presynthesized blocks rather than added nucleotide by nucleotide.

a. Synthesis of Protected Oligonucleotides

Using this procedure, PCR primer binding site oligonucleotides P1 and P2 were synthesized having the nucleotide sequences shown in Table 2, but having an DMT at the oligonucleotide's 5' terminus, and having a CNET ester and an amino diisopropyl phosphoramidate at the oligonucleotide's 3' terminus. Similarly, unit identifier oligonucleotides were synthesized for glycine (gly) and methionine (met) having 6 nucleotides per unit and having the blocked termini described above. The unit identifier oligonucleotide sequences are shown in Table 2.

TABLE 2

| Designation | SEQ ID NO | Oligonucleotide Sequence |
|---|---|---|
| P1 | 1 | 5'-GGGCCCTATTCTTAG-3' |
| P2 | 2 | 5'-AGCTACTTCCCAAGG-3' |
| $Z^{gly}$ | | 5'-CACATG-3' |
| $Z^{met}$ | | 5'-ACGGTA-3' | b. Synthesis of a Library

Figure 2:
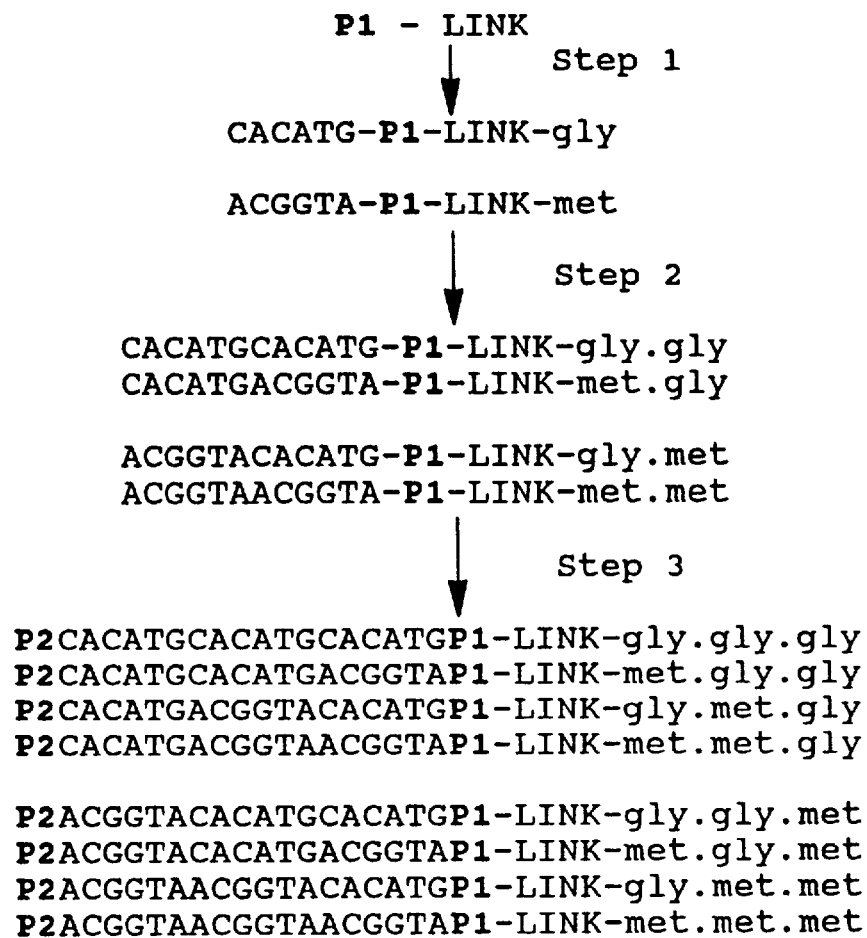
FIG. 2 illustrates the process of producing a library of bifunctional molecules according to the method described in Example 9. The nucleotide base sequences shown in FIG. 1 are listed in the Sequence Listing, SEQ ID Nos 15–22.

The synthesis of a prototype library is described where the chemical unit is an amino acid, the alphabet size is 2, being comprised of glycine and methionine, the unit identifier nucleotide sequence is 6 nucleotides in length, and the chemical polymer length is three amino acids in length. A schematic of the process is shown in FIG. 2.

The solid support prepared in Example 2 is coupled to the linker as described in Example 3. For convenience, the solid support-coupled linker molecule is referred to as LINK. Thereafter, protected oligonucleotide P1 is coupled to LINK as described for a single protected nucleotide in Example 4 to form the structure P1-LINK.

In Step 1, P1-LINK is divided into two aliquots.

The first aliquot is subjected to the sequential coupling of the amino acid residue glycine as described in Example 5, and then coupling of the protected oligonucleotide $Z^{gly}$ as described in Example 4 to form the structure CACATG-P1-LINK-gly. The second aliquot is similarly coupled to add the amino acid methionine and the oligonucleotide $Z^{met}$ to form the structure ACGGTA-P1-LINK-met. The two aliquots are then pooled to form a mixture of the two bifunctional molecules.

In Step 2, the pool from Step 1 is divided into two aliquots. The first aliquot is subjected to a sequential coupling as before, adding glycine and the oligonucleotide $Z^{gly}$ to form the structures:

CACATGCACATG-P1-LINK-gly.gly, and

CACATGACGGTA-P1-LINK-met.gly SEQ ID NOS 3 and 4

The second aliquot is subjected to a sequential coupling as before, adding methionine and the oligonucleotide $Z^{met}$ to form the structures:

ACGGTACACATG-P1-LINK-gly. SEQ ID NO:5met, and

ACGGTAACGGTA-P1-LINK-met.met. SEQ ID NO:6

The two aliquots are then pooled to form a mixture of the four bifunctional molecules.

In Step 3, the pool from Step 2 is divided into two aliquots. The first aliquot is subjected to a sequential coupling as before, adding glycine and the oligonucleotide $Z^{gly}$. Thereafter, protected oligonucleotide P2 is coupled to the growing bifunctional molecules in the pool as described for a single protected nucleotide in Example 4 to form the structures:

P2CACATGCACATGCACATGP1-LINK-gly.gly.gly, SEQ ID NO:7

P2CACATGCACATGACGGTAP1-LINK-met.gly.gly, SEQ ID NO:8

P2CACATGACGGTACACATGP1-LINK-gly.met.SEQ ID NO: 9gly, and

P2CACATGACGGTAACGGTAP1-LINK-met.met.gly.SEQ ID NO:10

The second aliquot is subjected to a sequential coupling as before, adding methionine and the oligonucleotide $Z^{met}$. Thereafter, protected oligonucleotide P2 is coupled to the growing bifunctional molecules in the pool as described for a single protected nucleotide in Example 4 to form the structures:

P2ACGGTACACATGCACATGP1-LINK-gly.gly.met SEQ ID NO:11,

P2ACGGTACACATGACGGTAP1-LINK-met.gly.met SEQ ID NO:12,

P2ACGGTAACGGTACACATGP1-LINK-gly.met.met SEQ ID NO:13, and

P2ACGGTAACGGTAACGGTAP1-LINK-met.met.met SEQ ID NO:14.

The two aliquots are then pooled to form a mixture of the eight bifunctional molecules.

The resulting pool of eight different bifunctional molecules represents a small library produced according to the methods of this invention. By increasing the alphabet size one increases the number of aliquots per step.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A bifunctional molecule according to the formula A—B—C, wherein A is a polymer comprising a linear series of chemical units represented by the formula $(X_n)_a$, wherein X is a single chemical unit in polymer A, B is a linker molecule operatively linked to A and C. and identifier oligonucleotide C is represented by the formula $(Z_n)_a$, wherein a unit identifier nucleotide sequence Z within oligonucleotide C identifies the chemical unit X at position n; and wherein n is a position identifier for both X in polymer A and Z in oligonucleotide C having the value of 1+i where i is an integer from 0 to 10, such that when n is 1, X or Z is located most proximal to the linker, and a is an integer from 4 to 50.

2. The bifunctional molecule of claim 1 wherein said unit identifier nucleotide sequence Z has a length of from 2 to 8 nucleotides.

3. The bifunctional molecule of claim 1 wherein said polymer is an oligosaccharide, polepeptide, glycolipid, lipid, proteoglycan, glycopeptide or oligonucleotide.

4. The bifunctional molecule of claim 1 wherein said polymer A is a polypeptide, X is an amino acid residue in said polypeptide, and unit identifier nucleotide sequence Z is a hexanucleotide sequence that identifies the amino acid residue at position n in polypeptide A.

5. The bifunctional molecule of claim 4 wherein said amino acid residue is selected from the group consisting of natural, modified and non-natural amino acids.

6. The bifunctional molecule of claim 1 wherein said identifier oligonucleotide C has a nucleotide sequence according to the formula P1—$(Z_n)_a$—P2, where P1 and P2 are nucleotide sequences that provide polymerase chain reaction (PCR) primer binding sites adapted to amplify the identifier oligonucleotide.

7. The bifunctional molecule of claim 6 wherein said P1 and P2 each contain a sequence that defines a restriction endonuclease site when present in a PCR-amplified duplex DNA fragment.

8. The bifunctional molecule of claim 7 wherein said restriction endonuclease sites are located proximal to $(Z_n)_a$ relative to the PCR primer binding sites.

9. The bifunctional molecule of claim 8 wherein said restriction endonuclease sites form non-overlapping cohesive termini upon restriction endonuclease cleavage.

10. A library comprising a plurality of species of bifunctional molecules according to claim 1.

11. The library of claim 10 wherein said plurality of species is defined by the formula $V^a$, where V represents the number of different chemical units forming an alphabet of possible chemical units of X, and a is an exponent to V and represents the number of chemical units of X forming polymer A.

12. The library of claim 11 wherein X is a natural amino acid and V is 20.

13. The library of claim 11 wherein the number of chemical units (a) forming polymer A is from about 3 to about 8.

14. The library of claim 12 wherein a is 6.

15. The library of claim 12 wherein X is an amino acid and identifier oligonucleotide C is represented by the formula $(Z_n)_a$ wherein a unit identifier nucleotide sequence Z within oligonucleotide C identifies the chemical unit X at position n: and wherein n is a position identifier for both X in polymer A and Z in oligonucleotide C having the value of 1+i where i is an integer from 0 to 10, such that when n is 1, X or Z is located most proximal to the linker, and a is an integer from 4 to 50 and said unit identifier nucleotide sequence Z has a length from 3 to 6 nucleotides.

16. The library of claim 10 wherein each of said species of bifunctional molecules in said plurality is present in molar equivalents of from 0.2 to 10.0.

17. The library of claim 11 wherein said identifier oligonucleotide in each of said species of bifunctional molecules has a nucleotide sequence according to the formula P1—$(Z_n)_a$—P2, where P1 and P2 are nucleotide sequences that provide PCR primer binding sites adapted to amplify the identifier oligonucleotide, and where the nucleotide sequences of P1 and P2 are shared by all bifunctional molecule species in the library.

* * * * *

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

GGGCCCTATT CTTAG                                                         15

(2) INFORMATION FOR SEQ ID NO:2:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

AGCTACTTCC CAAGG                                                         15

(2) INFORMATION FOR SEQ ID NO:3:

(i) SEQUENCE CHARACTERISTICS:
      (A) LENGTH: 13 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: misc_feature
      (B) LOCATION: 13
      (D) OTHER INFORMATION: /note= "N is P1 (SEQ ID NO 1)"

(xi) SEQUENCE DESCRIPTION: SEQ ID NO:3:

CACATGCACA TGN                                                            13

(2) INFORMATION FOR SEQ ID NO:4:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION: 13
        (D) OTHER INFORMATION: /note= "N is P1 (SEQ ID NO 1)"

(xi) SEQUENCE DESCRIPTION: SEQ ID NO:4:

CACATGACGG TAN                                                        13

(2) INFORMATION FOR SEQ ID NO:5:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION: 13
        (D) OTHER INFORMATION: /note= "N is P1 (SEQ ID NO 1)"

(xi) SEQUENCE DESCRIPTION: SEQ ID NO:5:

ACGGTACACA TGN                                                        13

(2) INFORMATION FOR SEQ ID NO:6:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION: 13
        (D) OTHER INFORMATION: /note= "N is P1 (SEQ ID NO 1)"

(xi) SEQUENCE DESCRIPTION: SEQ ID NO:6:

ACGGTAACGG TAN                                                        13

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear

```
    (ii) MOLECULE TYPE: DNA (genomic)

(iii) HYPOTHETICAL: NO (iv) ANTI-SENSE: NO (ix) FEATURE:
         (A) NAME/KEY: misc_feature
         (B) LOCATION: 1
         (D) OTHER INFORMATION: /note= "N is P2 (SEQ ID NO 2)"

(ix) FEATURE:
         (A) NAME/KEY: misc_feature
         (B) LOCATION: 20
         (D) OTHER INFORMATION: /note= "N is P1 (SEQ ID NO 1)"

(xi) SEQUENCE DESCRIPTION: SEQ ID NO:7:

NCACATGCAC ATGCACATGN                                               20

(2) INFORMATION FOR SEQ ID NO:8:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (ix) FEATURE:
         (A) NAME/KEY: misc_feature
         (B) LOCATION: 1
         (D) OTHER INFORMATION: /note= "N is P2 (SEQ ID NO 2)"

(ix) FEATURE:
         (A) NAME/KEY: misc_feature
         (B) LOCATION: 20
         (D) OTHER INFORMATION: /note= "N is P1 (SEQ ID NO 1)"

(xi) SEQUENCE DESCRIPTION: SEQ ID NO:8:

NCACATGCAC ATGACGGTAN                                               20

(2) INFORMATION FOR SEQ ID NO:9:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (ix) FEATURE:
         (A) NAME/KEY: misc_feature
         (B) LOCATION: 1
         (D) OTHER INFORMATION: /note= "N is P2 (SEQ ID NO 2)"

(ix) FEATURE:
         (A) NAME/KEY: misc_feature
         (B) LOCATION: 20
         (D) OTHER INFORMATION: /note= "N is P1 (SEQ ID NO 1)"

(xi) SEQUENCE DESCRIPTION: SEQ ID NO:9:

NCACATGACG GTACACATGN                                               20
```

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION: 1
        (D) OTHER INFORMATION: /note= "N is P2 (SEQ ID NO 2)"

(ix) FEATURE:
        (A) NAME/KEY: misc_feature
        (B) LOCATION: 20
        (D) OTHER INFORMATION: /note= "N is P1 (SEQ ID NO 1)"

(xi) SEQUENCE DESCRIPTION: SEQ ID NO:10:

NCACATGACG GTAACGGTAN                         20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION: 1
        (D) OTHER INFORMATION: /note= "N is P2 (SEQ ID NO 2)"

(ix) FEATURE:
        (A) NAME/KEY: misc_feature
        (B) LOCATION: 20
        (D) OTHER INFORMATION: /note= "N is P1 (SEQ ID NO 1)"

(xi) SEQUENCE DESCRIPTION: SEQ ID NO:11:

NACGGTACAC ATGCACATGN                         20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION: 1
        (D) OTHER INFORMATION: /note= "N is P2 (SEQ ID NO 2)"

(ix) FEATURE:

```
        (A) NAME/KEY: misc_feature
        (B) LOCATION: 20
        (D) OTHER INFORMATION: /note= "N is P1 (SEQ ID NO 1)"

(xi) SEQUENCE DESCRIPTION: SEQ ID NO:12:

NACGGTACAC ATGACGGTAN                                                    20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION: 1
        (D) OTHER INFORMATION: /note= "N is P2 (SEQ ID NO 2)"

(ix) FEATURE:
        (A) NAME/KEY: misc_feature
        (B) LOCATION: 20
        (D) OTHER INFORMATION: /note= "N is P1 (SEQ ID NO 1)"

(xi) SEQUENCE DESCRIPTION: SEQ ID NO:13:

NACGGTAACG GTACACATGN                                                    20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION: 1
        (D) OTHER INFORMATION: /note= "N is P2 (SEQ ID NO 2)"

(ix) FEATURE:
        (A) NAME/KEY: misc_feature
        (B) LOCATION: 20
        (D) OTHER INFORMATION: /note= "N is P1 (SEQ ID NO 1)"

(xi) SEQUENCE DESCRIPTION: SEQ ID NO:14:

NACGGTAACG GTAACGGTAN                                                    20

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO
```

(iv) ANTI-SENSE: NO (ix) FEATURE:
        (A) NAME/KEY: misc_feature
        (B) LOCATION: (15^16)
        (D) OTHER INFORMATION: /note= "Coding sequence located at
            indicated position"

(xi) SEQUENCE DESCRIPTION: SEQ ID NO:15:

AGCTACTTCC CAAGGGGGCC CTATTCTTAG                                    30

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION: (15^16)
        (D) OTHER INFORMATION: /note= "Anticoding sequence located
            at indicated position"

(xi) SEQUENCE DESCRIPTION: SEQ ID NO:16:

CTAAGAATAG GGCCCCCTTG GGAAGTAGCT                                    30

(2) INFORMATION FOR SEQ ID NO:17:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:17:

AGCTACTTCC                                                          10

(2) INFORMATION FOR SEQ ID NO:18:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION: (5^6)
        (D) OTHER INFORMATION: /note= "Coding sequence located at
            indicated position"

(xi) SEQUENCE DESCRIPTION: SEQ ID NO:18:

```
CAAGGGGGCC                                                                      10

(2) INFORMATION FOR SEQ ID NO:19:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:19:

CTATTCTTAG                                                                      10

(2) INFORMATION FOR SEQ ID NO:20:

(i) SEQUENCE CHARACTERISTICS:
           (A) LENGTH: 14 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:20:

CTAAGAATAG GGCC                                                                 14

(2) INFORMATION FOR SEQ ID NO:21:

(i) SEQUENCE CHARACTERISTICS:
           (A) LENGTH: 14 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:21:

CTTGGGAAGT AGCT                                                                 14

(2) INFORMATION FOR SEQ ID NO:22:

(i) SEQUENCE CHARACTERISTICS:
           (A) LENGTH: 11 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:22:

AGCTACTTCC C                                                                    11
```